United States Patent
Sawayanagi (10) Patent No.: US 9,940,740 B2
(45) Date of Patent: Apr. 10, 2018

(54) REFRACTOMETER

(71) Applicant: SHIMADZU CORPORATION, Kyoto-shi, Kyoto (JP)

(72) Inventor: Nobuhiko Sawayanagi, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 90 days.

(21) Appl. No.: 14/900,371

(22) PCT Filed: Jun. 24, 2013

(86) PCT No.: PCT/JP2013/067270
§ 371 (c)(1),
(2) Date: Dec. 21, 2015

(87) PCT Pub. No.: WO2014/207809
PCT Pub. Date: Dec. 31, 2014

(65) Prior Publication Data
US 2016/0163077 A1   Jun. 9, 2016

(51) Int. Cl.
*G06T 11/20* (2006.01)
*G01N 21/41* (2006.01)

(52) U.S. Cl.
CPC ........ *G06T 11/206* (2013.01); *G01N 21/4133* (2013.01)

(58) Field of Classification Search
None
See application file for complete search history.

(56) References Cited

U.S. PATENT DOCUMENTS

| | | | |
|---|---|---|---|
| 6,172,746 B1 | 1/2001 | Byrne et al. | |
| 2007/0282206 A1* | 12/2007 | Arnone | A61B 5/0059 600/473 |
| 2010/0207036 A1* | 8/2010 | Massonneau | A61B 5/0059 250/459.1 |
| 2011/0051127 A1* | 3/2011 | Kusaka | G01M 11/0228 356/128 |

(Continued)

FOREIGN PATENT DOCUMENTS

| | | |
|---|---|---|
| JP | 58-200209 A | 11/1983 |
| JP | S63-188744 A | 8/1988 |

(Continued)

OTHER PUBLICATIONS

International Search Report for PCT/JP2013/067270 dated Sep. 10, 2013 [PCT/ISA/210].

*Primary Examiner* — James A Thompson
(74) *Attorney, Agent, or Firm* — Sughrue Mion, PLLC (57) ABSTRACT

The present invention aims to provide a refractometer that can satisfactorily observe an actual state of measurement light during a measurement with low cost. A graph 311 showing detection intensity of measurement light detected by a detector and a captured image 312 by a camera are displayed on one display screen 301 in real time. This configuration eliminates the need to separately provide a display unit for displaying the captured image 312 by the camera, thereby reducing cost. In addition, the actual state of measurement light can satisfactorily be observed during the measurement through the confirmation of the captured image 312 by the camera displayed on one display screen 301 along with the graph 311 in real time.

5 Claims, 4 Drawing Sheets

(56) References Cited

U.S. PATENT DOCUMENTS

| | | | | |
|---|---|---|---|---|
| 2012/0229411 A1* | 9/2012 | Arai | ..................... | G06F 3/0488 |
| | | | | 345/173 |
| 2013/0027696 A1 | 1/2013 | Sekiyama | | |
| 2013/0182245 A1* | 7/2013 | Yasunaga | ............... | G01N 21/41 |
| | | | | 356/135 |
| 2013/0208266 A1* | 8/2013 | Yoon | .................. | G01N 21/4133 |
| | | | | 356/128 |
| 2015/0160124 A1* | 6/2015 | Ho | .................... | G01L 39/02091 |
| | | | | 702/189 |
| 2016/0123873 A1* | 5/2016 | Cook | .................... | G01M 11/37 |
| | | | | 356/73.1 |
| 2017/0017071 A1* | 1/2017 | Ue | ........................ | G06T 11/206 |

FOREIGN PATENT DOCUMENTS

| | | |
|---|---|---|
| JP | 10-48056 A | 2/1998 |
| JP | 2000-356558 A | 12/2000 |
| JP | 2001-165854 A | 6/2001 |
| JP | 2002-207004 A | 7/2002 |
| JP | 2011-99795 A | 5/2011 |
| JP | 2011-193752 A | 10/2011 |
| JP | 2011-220903 A | 11/2011 |
| JP | 2013-29322 A | 2/2013 |

\* cited by examiner

REFRACTOMETER

CROSS REFERENCE TO RELATED APPLICATIONS

This application is a National Stage of International Application No. PCT/JP2013/067270, filed on Jun. 24, 2013, the contents of all of which are incorporated herein by reference in their entirety.

TECHNICAL FIELD

The present invention relates to a refractometer that measures a refractive index of a sample by irradiating the sample with measurement light.

BACKGROUND ART

In a V-block refractometer which is one example of refractometers, a sample is placed on a V-shaped groove formed on a V-block prism, and the sample is irradiated with measurement light through the V-block prism. The measurement light passing through the sample is detected by a detector, whereby a refractive index of the sample can be measured (see Patent Document 1 below, for example).

With the refractometer of this type, a part of measurement light passing through a sample to be guided to a detector is split by a beam splitter, for example, and guided to an eyepiece unit (not illustrated). When performing a work for adjusting the position of the V-block prism, or the like, an operator can perform the work, while visually recognizing the state of the measurement light, by seeing the inside of the refractometer from the eyepiece unit.

PRIOR ART DOCUMENTS

Patent Documents

Patent Document 1: JP 2011-99795 A

SUMMARY OF THE INVENTION

Problems to be Solved by the Invention

In the conventional V-block refractometer described above, a cap is placed on the eyepiece unit during the measurement in order to prevent incident light from the outside of the refractometer through the eyepiece unit from adversely affecting the detection result by the detector. Accordingly, the conventional refractometer entails a problem such that the actual state of the measurement light cannot be observed during the measurement.

To address this problem, such configuration is considered that a camera is mounted to the eyepiece unit to prevent incidence of light from the outside of the refractometer through the eyepiece unit and to capture the measurement light by the camera at the eyepiece unit, in order to enable observation of the image captured by the camera during the measurement. However, when a camera is attached later to a refractometer as described above, a display unit for displaying an image captured by the camera has to be additionally mounted, which increases cost. Further, since the detection result by the detector and the image captured by the camera are displayed on different display screens, smooth observation might not be performed.

The present invention is accomplished in view of the above circumstances, and aims to provide a refractometer that can satisfactorily observe an actual state of measurement light during a measurement with low cost. The present invention also aims to provide a refractometer that can satisfactorily perform a measurement.

Means for Solving the Problems

The refractometer according to the present invention is a refractometer that measures a refractive index of a sample by irradiating the sample with measurement light, the refractometer comprising: a detector that detects measurement light passing through the sample; a camera that captures measurement light passing through the sample; and a display processing unit that displays a graph indicating detection intensity of measurement light detected by the detector and an image of measurement light captured by the camera on one display screen in real time.

According to this configuration, the graph indicating the detection intensity of the measurement light detected by the detector and the image of measurement light captured by the camera are displayed on one display screen in real time. Therefore, there is no need to separately provide a display unit for displaying the captured image by the camera, whereby cost can be reduced. In addition, the actual state of measurement light can satisfactorily be observed during the measurement through the confirmation of the captured image by the camera displayed on one display screen along with the graph in real time.

For example, when performing a work for adjusting the position of a V-block prism, or the like, an operator can perform the work, while confirming the captured image by the camera displayed on the display screen in real time. The configuration in which the captured image by the camera is displayed on the display screen as described above eliminates the need to provide an eyepiece unit. Accordingly, this configuration can prevent incident light from the outside of the refractometer through the eyepiece unit from adversely affecting the detection result by the detector during the measurement, whereby the measurement can satisfactorily be performed.

In addition, how much the measurement light blurs can be observed during the measurement through the confirmation of the captured image by the camera displayed on the display screen in real time. When a sample is not appropriately placed, or when a sample has property of being likely to diffuse light, measurement light is likely to be blurred. Through the real-time confirmation of the degree of blur of the measurement light along with the graph, satisfactory measurement can be attained.

The refractometer may further comprise a scanning processing unit that performs scanning by changing an angle at which measurement light emitted from the sample is received or an angle of measurement light incident on the sample. In this case, it is preferable that the display processing unit displays detection intensity by the detector on the display screen in real time as being continuously depicted as a graph, the detection intensity being changed with scanning by the scanning processing unit, and the display processing unit also displays an image captured by the camera on the display screen in real time so as to move with scanning.

According to this configuration, the operator can confirm the graph continuously depicted on the display screen with the scanning, and can also confirm the captured image by the camera at that time in real time on the same display screen. Accordingly, the relationship between the detection intensity of the measurement light detected by the detector and the captured image by the camera is easy-to-follow, whereby the measurement can more satisfactorily be performed.

It is preferable that the display processing unit displays on the display screen an image-capture switch key for starting or stopping a display of an image captured by the camera on the display screen.

According to this configuration, the display of the captured image by the camera on the display screen can be started or stopped through the selection of the image-capture switch key according to need. With this, the graph and the captured image by the camera are displayed on one display screen in real time only when necessary, such as during the measurement. Thus, measurement can satisfactorily be performed.

It is preferable that the display processing unit displays on the display screen an enlarged display key for enlarging and displaying an image captured by the camera on another screen on the display screen.

According to this configuration, the captured image by the camera can be displayed as enlarged on another screen on the display screen through the selection of the enlarged display key according to need. With this, when the position of the V-block prism is intended to be adjusted more accurately or when the degree of blur of measurement light is intended to be observed more accurately, the captured image by the camera is confirmed with the enlarged display, by which such work can satisfactorily be performed.

It is preferable that the display processing unit displays on the display screen a stop key for stopping scanning by the scanning processing unit.

According to this configuration, the scanning by the scanning processing unit can be stopped to stop the measurement through the selection of the stop key as necessary. Therefore, when recognizing abnormality upon confirming the graph continuously depicted on the display screen with the scanning and also confirming the captured image by the camera at that time on the same display screen in real time, the operator can immediately stop the measurement. Thus, the measurement can more satisfactorily be performed.

Effects of the Invention

The present invention eliminates the need to separately provide a display unit for displaying a captured image by a camera, thereby reducing cost. In addition, according to the present invention, the actual state of measurement light can satisfactorily be observed during a measurement through the confirmation of a captured image by a camera displayed on one display screen along with a graph in real time. Furthermore, according to the present invention, light outside the refractometer is not incident from an eyepiece unit during a measurement, and a degree of blur of measurement light can be confirmed in real time along with a graph, whereby the measurement can satisfactorily be performed.

MODE FOR CARRYING OUT THE INVENTION

Figure 1:
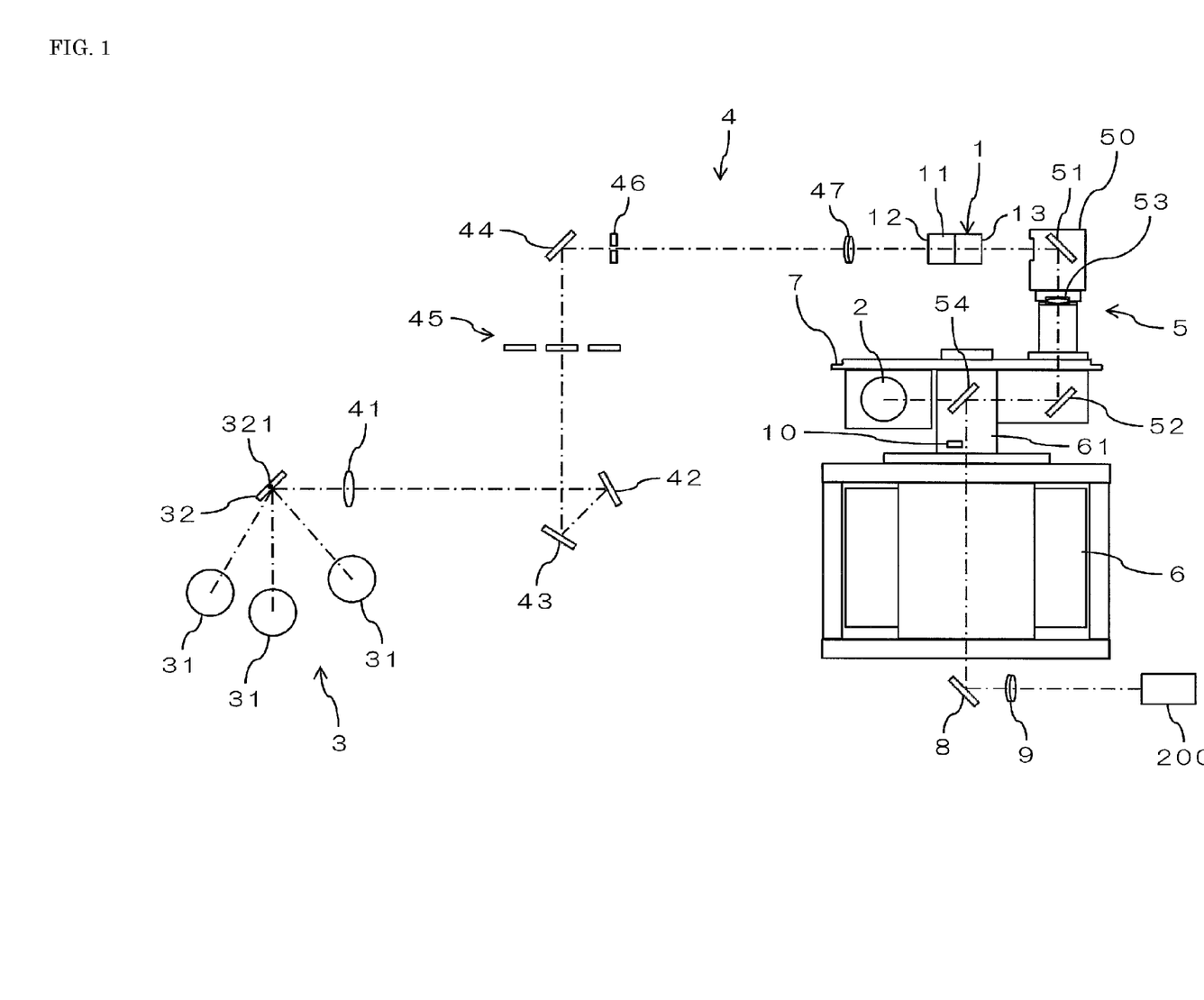
FIG. 1 is a schematic plan view illustrating an example of a configuration of a refractometer according to one embodiment of the present invention.

FIG. 1 is a schematic plan view illustrating an example of a configuration of a refractometer according to one embodiment of the present invention. This refractometer is a V-block refractometer that measures a refractive index of a sample by irradiating the sample with measurement light through a V-block prism 1.

Examples of the sample include glass, plastic, and liquid. The sample is placed on a V-shaped groove 11 formed on the V-block prism 1 (FIG. 1 illustrates a view when the groove 11 is viewed from straight above), and the refractive index of the sample can be measured by detecting measurement light passing through the sample by a detector 2.

The refractometer includes, in addition to the above V-block prism 1 and the detector 2, a light source unit 3 that emits measurement light, a first optical system 4 that guides the measurement light from the light source unit 3 to the V-block prism 1, and a second optical system 5 that guides the measurement light passing through the V-block prism 1 to the detector 2.

The light source unit 3 includes a plurality of light sources 31. A helium lamp, a hydrogen lamp, or a mercury lamp is used for the light sources 31, and measurement lights, each having a different wavelength such as helium d line, hydrogen C line, hydrogen F line, mercury e line, mercury g line, and mercury h line, can be emitted from the light source unit 3. The measurement light from the light sources 31 is reflected on a mirror 32, and emitted in the horizontal direction from the light source unit 3. The mirror 32 is rotatable about a rotation shaft 321 extending in the perpendicular direction (front-to-back direction of the sheet of FIG. 1), and capable of guiding measurement light from the light source 31 according to the rotation position of the mirror 32 toward the first optical system 4. Notably, the light sources 31 are not limited to the above types.

The first optical system 4 includes a lens 41, mirrors 42, 43, and 44, an interference filter 45, a slit 46, a collimator lens 47, and the like. Measurement light from the light source unit 3 passes through the lens 41, is sequentially reflected on the mirrors 42 and 43, and then, incident on the interference filter 45.

Two or more of the interference filters 45 are provided. The interference filter 45 selected according to the type of the light sources 31 is interposed on the optical path, whereby only the measurement light (monochromatic light) having a specific wavelength corresponding to the selected interference filter 45 passes through the interference filter 45 and is guided toward the mirror 44. The measurement light reflected on the mirror 44 passes through the slit 46, is converted into parallel light by the collimator lens 47, and incident on the V-block prism 1. Measurement light incident on one end face 12 of the V-block prism 1 passes through the sample placed on the V-shaped groove 11, passes again through the V-block prism 1, and is emitted from the other end face 13 at an angle corresponding to the difference in refractive index between the V-block prism 1 and the sample.

The second optical system 5 includes mirrors 51 and 52, a telemeter lens 53, a beam splitter 54, and the like. The second optical system 5 is fixed to a circular disc 7 mounted to a rotation shaft 61 of a motor 6. Specifically, the mirrors 51 and 52 and the telemeter lens 53 are arranged parallel to the rotation shaft 61 at an eccentric position relative to the rotation shaft 61, and the mirror 52 and the beam splitter 54 are fixed to the circular disc 7 so as to be arranged vertically in a row relative to the rotation shaft 61.

The mirror 51 is disposed such that the reflection plane tilts at 45 degrees relative to the incidence direction of the measurement light. With this, the measurement light reflected on the mirror 51 changes its advancing direction by 90 degrees, and then, is guided to the telemeter lens 53. The telemeter lens 53 converges the measurement light from the V-block prism 1 and guides the resultant measurement light to the mirror 52. The measurement light reflected on the mirror 52 passes through the beam splitter 54, and is detected by the detector 2 fixed on the circular disc 7.

The mirror 51 and the telemeter lens 53 are arranged vertically in a row relative to the incidence direction of the measurement light from the V-block prism 1, and integrally held on the circular disc 7 as a telemeter unit 50 at an eccentric position relative to the rotation shaft 61. With this, when the circular disc 7 is rotated about the rotation shaft 61 with the rotation of the motor 6, the position of the telemeter unit 50 to the V-block prism 1 can be changed (scanned), whereby the telemeter unit 50 can receive the measurement light from the V-block prism 1 at different angles, and guide the received measurement light to the detector 2. The motor 6 is a servo motor with an encoder, for example, and can accurately measure the rotation angle of the motor 6.

On the other hand, the measurement light reflected on the beam splitter 54 is reflected on a mirror 8, and then, passes through a lens 9 to be guided toward a camera 200 which can capture the measurement light passing through the sample. The beam splitter 54 and the mirror 8 are provided on the rotation shaft 61. When the position of the V-block prism 1 is to be adjusted, an auto collimation prism 10 can be interposed on the optical path between the beam splitter 54 and the mirror 8.

The camera 200 can be composed of a CCD (Charge Coupled Device) camera, for example. The camera 200 is not limited to be mounted on the above position. For example, the camera 200 may be mounted on the circular disc 7, and measurement light may be guided to the camera 200 through a beam splitter mounted separately from the beam splitter 54. Alternatively, two or more cameras 200 may be mounted.

Figure 2:
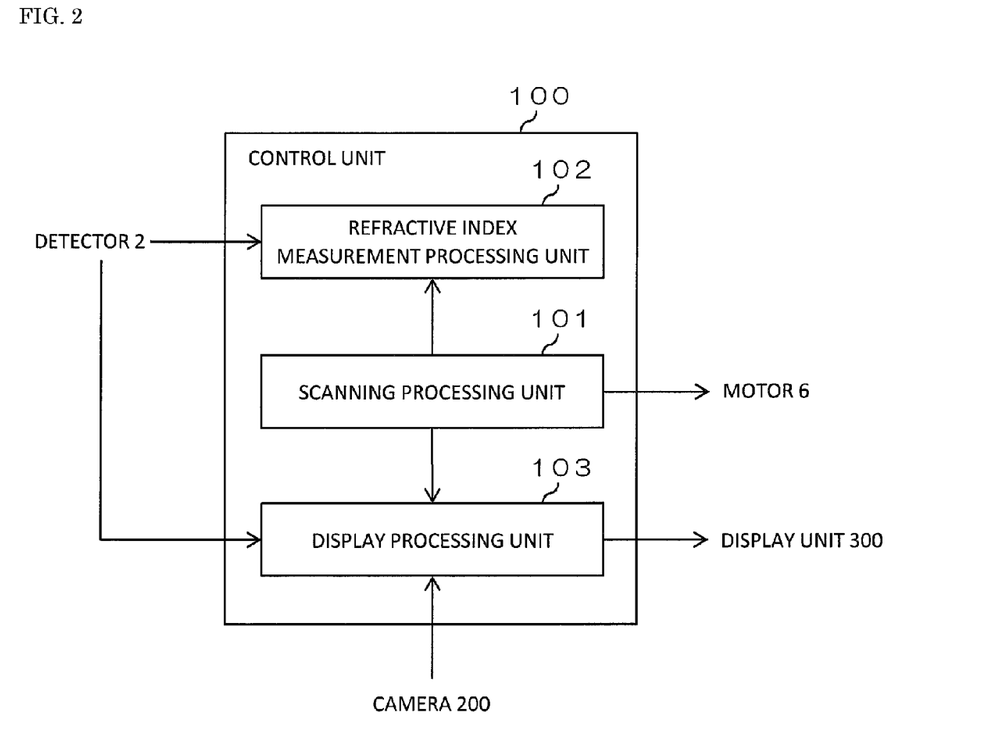
FIG. 2 is a block diagram illustrating an example of a configuration of a control unit in the refractometer illustrated in FIG. 1.

FIG. 2 is a block diagram illustrating an example of a configuration of a control unit 100 in the refractometer illustrated in FIG. 1. The operation of the refractometer is controlled by the control unit 100 including a CPU (Central Processing Unit), for example. The control unit 100 functions as a scanning processing unit 101, a refractive index measurement processing unit 102, and a display processing unit 103 through the execution of a program by the CPU.

The scanning processing unit 101 allows the telemeter unit 50 to perform scanning relative to the V-block prism 1 by rotating the motor 6. Upon a measurement of a refractive index of a sample, the scanning processing unit 101 rotates the motor 6 at constant speed to change the angle at which the measurement light emitted from the sample is received. With this, the quantity of the measurement light guided to the detector 2 from the V-block prism 1 is changed, resulting in that the detection intensity by the detector 2 is changed with the rotation of the motor 6.

The refractive index measurement processing unit 102 performs a process for measuring a refractive index of a sample based on a rotation angle of the motor 6 rotated by the scanning processing unit 101 and detection intensity by the detector 2. Specifically, the measurement light from the V-block prism 1 at each rotation angle is detected by the detector 2 by rotating the motor 6. With this, the rotation angle at which the detection intensity becomes the highest can be specified, and the refractive index of the sample can be measured based on this rotation angle and the refractive index of the V-block prism 1.

The display processing unit 103 performs a process relating to a display on a display screen of a display unit 300. The display unit 300 includes a liquid crystal display device, for example. The display unit 300 may be provided to the refractometer, or may be provided separately from the refractometer. The display processing unit 103 can display the relation between the rotation angle of the motor 6 rotated by the scanning processing unit 101 and the detection intensity by the detector 2 on the display screen of the display unit 300 in the form of a graph, for example. The display processing unit 103 can also display an image of measurement light captured by the camera 200 on the display screen of the display unit 300.

Figure 3:
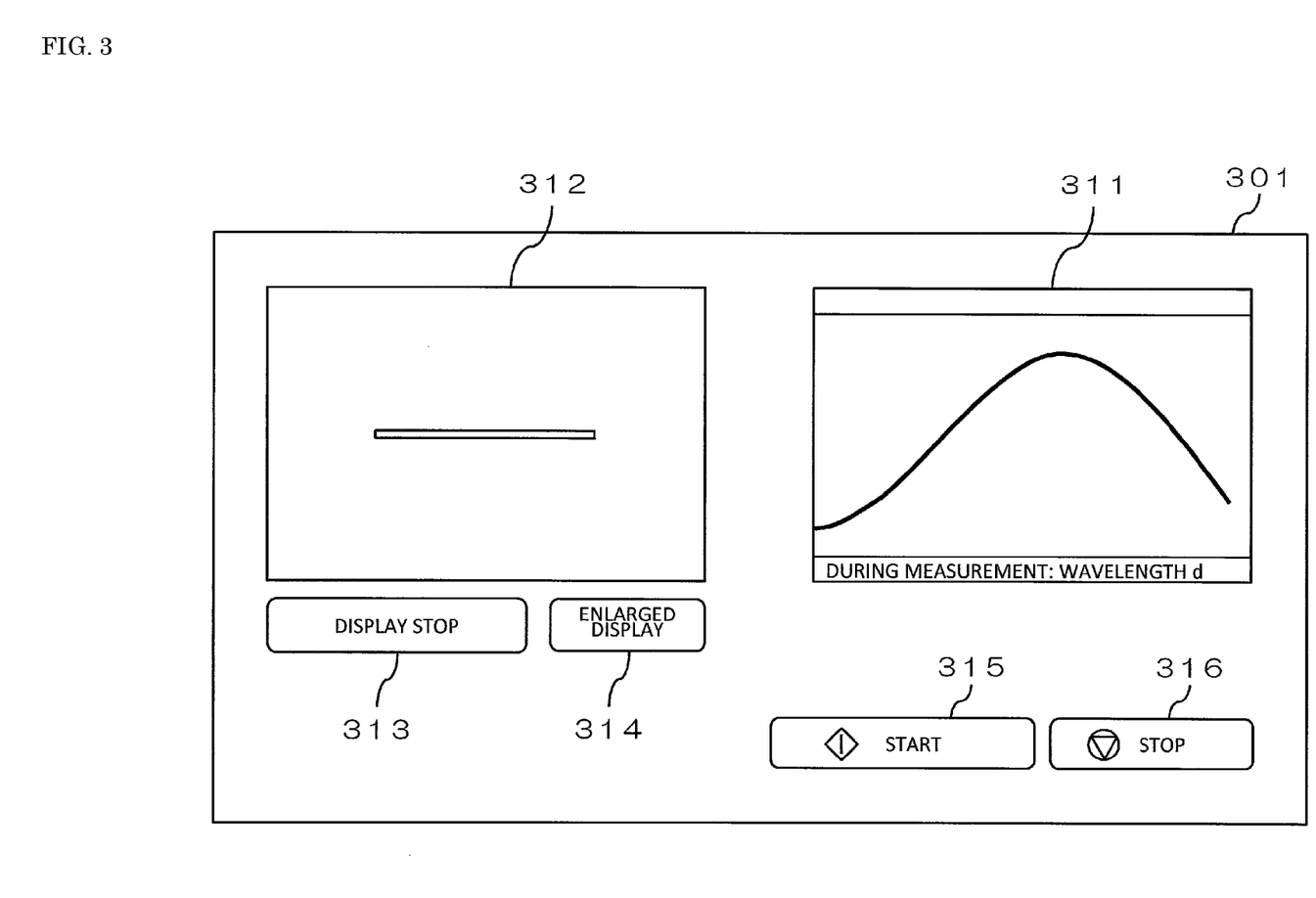
FIG. 3 is a view illustrating one example of the display screen of the display unit.

FIG. 3 is a view illustrating one example of the display screen 301 of the display unit 300. As illustrated in FIG. 3, in the present embodiment, a graph 311 showing detection intensity of measurement light detected by the detector 2 and a captured image 312 by the camera 200 are displayed on one display screen 301 in real time.

The graph 311 is displayed on the display screen 301 with a horizontal axis indicating the rotation angle of the motor 6 and a vertical axis indicating the detection intensity by the detector 2, for example. The captured image 312 by the camera 200 is an image of measurement light passing through the slit 46. Therefore, as illustrated in FIG. 3, the image 312 is displayed on the display screen 301 as a linear image corresponding to the shape of the slit 46, for example.

In this example, one linear image of measurement light is displayed as the captured image 312 by the camera 200. However, when a sample is a birefringent material, for example, measurement light passing through the sample emits in multiple directions, so that multiple linear images of measurement light are sometimes displayed. When the position of the V-block prism 1 is to be adjusted using the auto collimation prism 10, an auto collimation image of which display position is changed corresponding to the position of the V-block prism 1 and a gauge line appear in the captured image 312. The displayed auto collimation image and the gauge line are aligned to have a predetermined arrangement, whereby the position of the V-block prism 1 and the optical axis can be adjusted to be perpendicular to each other.

An image-capture switch key 313, an enlarged display key 314, a start key 315, a stop key 316, and the like are displayed on the display screen 301 with the process of the display processing unit 103. The image-capture switch key 313 and the enlarged display key 314 are displayed near the captured image 312 by the camera 200, for example. These keys 313 to 316 can be selected through an operation of an operation unit (not illustrated) including a mouse or a keyboard.

The image-capture switch key 313 is selected to start or stop the display of the captured image 312 by the camera 200 on the display screen 301. As illustrated in FIG. 3, when the captured image 312 by the camera 200 is displayed on the display screen 301, the image-capture switch key 313 is displayed as a display stop key. The display of the captured image 312 can be stopped through the selection of the display stop key. On the other hand, when the captured image 312 by the camera 200 is not displayed on the display screen 301, the image-capture switch key 313 is displayed as a display start key. The display of the captured image 312 can be started through the selection of the display start key.

The enlarged display key 314 is selected to enlarge and display the captured image 312 by the camera 200 on another screen on the display screen 301. When the enlarged display key 314 is selected, a pop-up screen is displayed on the display screen 301, for example, and the enlarged captured image 312 by the camera 200 is displayed on the pop-up screen with the horizontal to vertical ratio being maintained.

The start key 315 is selected to start the scanning by the scanning processing unit 101. When the measurement is started with the selection of the start key 315, the graph 311 and the captured image 312 by the camera 200 are displayed on the display screen 301 in real time with the scanning by the scanning processing unit 101. Notably, it may be configured such that the selection of the start key 315 is disabled during the measurement.

The stop key 316 is selected to stop the scanning by the scanning processing unit 101. When the stop key 316 is selected during the measurement, the measurement is stopped, and the display of the graph 311 and the captured image 312 by the camera 200 on the display screen 301 is stopped. Notably, it may be configured such that the selection of the stop key 316 is disabled when the measurement is not performed.

In the present embodiment, the graph 311 indicating the detection intensity of the measurement light detected by the detector 2 and the captured image 312 by the camera 200 are displayed on one display screen 301 in real time. Therefore, there is no need to separately provide a display unit for displaying the captured image 312 by the camera 200, whereby cost can be reduced. In addition, the actual state of the measurement light can satisfactorily be observed during the measurement through the confirmation of the captured image 312 by the camera 200 displayed on one display screen 301 along with the graph 311 in real time.

When performing a work for adjusting the position of the V-block prism 1, or the like, the operator can perform the work, while confirming the captured image 312 by the camera 200 displayed on the display screen 301 in real time. The configuration in which the captured image 312 by the camera 200 is displayed on the display screen 301 as described above eliminates the need to provide an eyepiece unit. Accordingly, this configuration can prevent incident light from the outside of the refractometer through the eyepiece unit from adversely affecting the detection result by the detector 2 during the measurement, whereby the measurement can satisfactorily be performed.

In addition, how much the measurement light blurs can be observed during the measurement through the confirmation of the captured image 312 by the camera 200 displayed on the display screen 301 in real time. When a sample is not appropriately placed, or when a sample has property of being likely to diffuse light, measurement light is likely to be blurred. Through the real-time confirmation of the degree of blur of the measurement light along with the graph 311, satisfactory measurement can be attained.

Especially in the present embodiment, the display of the captured image 312 by the camera 200 on the display screen 301 can be started or stopped through the selection of the image-capture switch key 313 according to need. With this, the graph 311 and the captured image 312 by the camera 200 are displayed on one display screen 301 in real time only when necessary, such as during the measurement. Thus, the measurement can satisfactorily be performed.

In addition, in the present embodiment, the captured image 312 by the camera 200 can be displayed as enlarged on another screen on the display screen 301 through the selection of the enlarged display key 314 according to need. With this, when the position of the V-block prism 1 is intended to be adjusted more accurately or when the degree of blur of measurement light is intended to be observed more accurately, for example, the captured image 312 by the camera 200 is confirmed with the enlarged display, by which such work can satisfactorily be performed.

Figure 4:
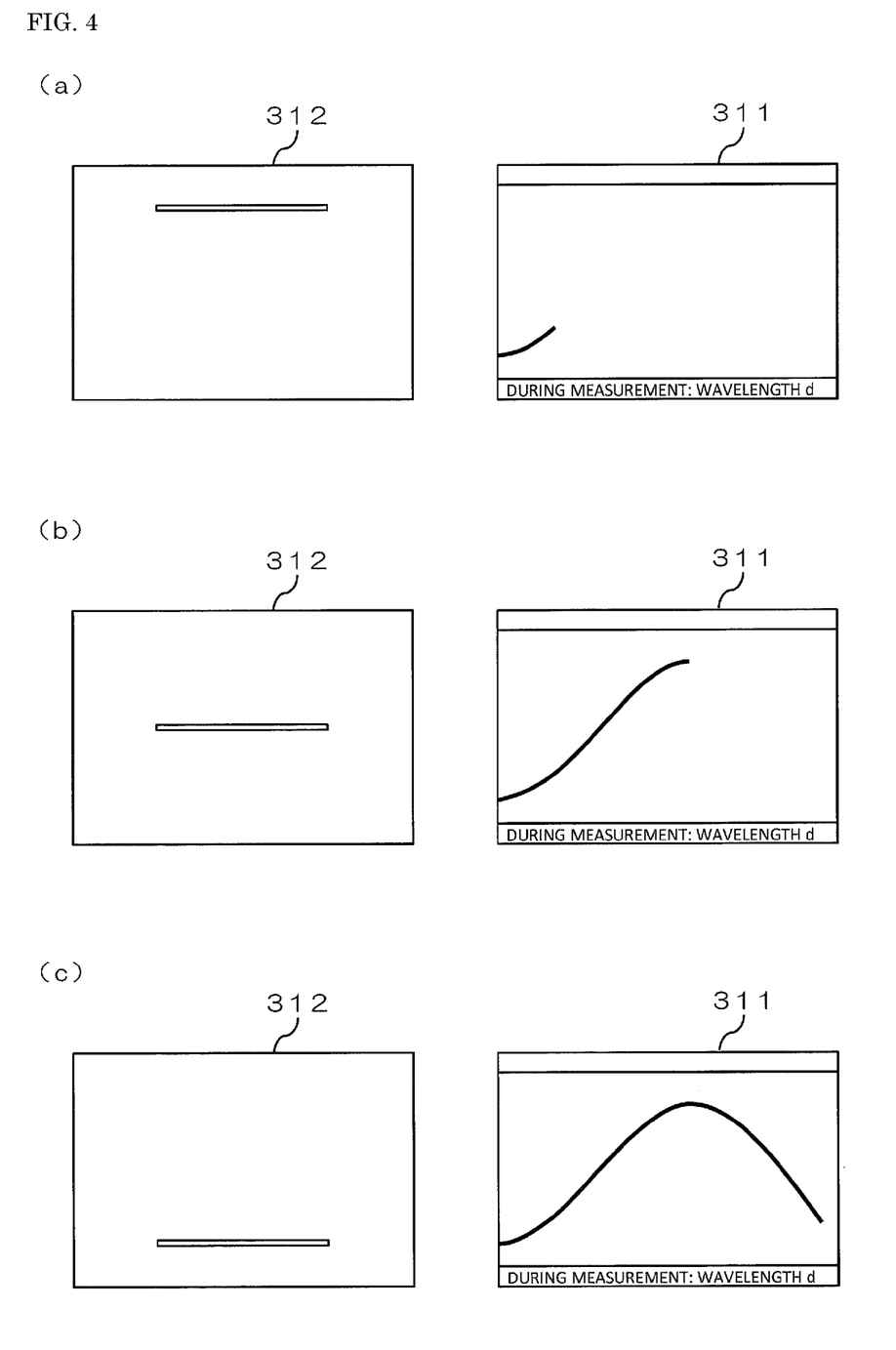
FIG. 4 is a view illustrating one example of a change of a display manner of the display screen of the display unit.

FIG. 4 is a view illustrating one example of a change of a display manner of the display screen 301 of the display unit 300. FIG. 4 illustrates one example of the graph 311 and the captured image 312 by the camera 200, which are displayed on the display screen 301 in real time during the measurement of a refractive index of a sample, in a stepwise manner.

The display processing unit 103 displays the detection intensity by the detector 2 on the display screen 301 in real time as being continuously depicted as the graph 311, the detection intensity changing with the scanning by the scanning processing unit 101. Specifically, the detection intensity by the detector 2 changes with the scanning by the scanning processing unit 101, and the trajectory of the change in the detection intensity from the start of the measurement to the present point is continuously depicted on the display screen 301 as the graph 311.

Therefore, in the initial stage after the start of the measurement, the part illustrated as the graph 311 is a few as illustrated in FIG. 4(*a*). However, when the detection intensity by the detector 2 becomes the highest as illustrated in FIG. 4(*b*), a peak appears on the graph 311. Thereafter, as the detection intensity by the detector 2 gradually decreases, the curved graph 311 with the peak is continuously depicted as illustrated in FIG. 4(*c*).

In addition, the display processing unit 103 displays the captured image 312 by the camera 200 in real time on the display screen 301 so as to move with the scanning. Specifically, since the angle at which the measurement light emitted from the sample is received is changed according to the scanning by the scanning processing unit 101, the position of the measurement light incident on the camera 200 is also changed, and the captured image 312 by the camera 200 moves on the display screen 301 as illustrated in FIGS. 4(*a*) to (*c*).

After the scanning by the scanning processing unit 101 is ended, the telemeter unit 50 is moved to the position where the detection intensity by the detector 2 becomes the highest, so that the captured image 312 by the camera 200 is maintained with the state illustrated in FIG. 4(*b*). In this case, the graph 311 may be maintained with the state illustrated in FIG. 4(*c*) or may not be displayed.

In the present embodiment, the operator can confirm the graph 311 continuously depicted on the display screen 301 with the scanning, and also confirm the captured image 312 by the camera 200 at that time in real time on the same display screen 301. Accordingly, the relationship between the detection intensity of the measurement light detected by the detector 2 and the captured image 312 by the camera 200 is easy-to-follow, whereby the measurement can more satisfactorily be performed.

In addition, in the present embodiment, the scanning by the scanning processing unit 101 can be stopped to stop the measurement through the selection of the stop key 316 as necessary, as described with reference to FIG. 3. Therefore, when recognizing abnormality upon confirming the graph 311 continuously depicted on the display screen 301 with the scanning and also confirming the captured image 312 by the camera 200 at that time on the same display screen 301 in real time, the operator can immediately stop the measurement. Thus, the measurement can more satisfactorily be performed.

The above embodiment describes the configuration in which measurement light is guided to the detector 2 from the light source unit 3 along the horizontal direction. However, the configuration is not limited thereto. At least a part of the optical path of the measurement light from the light source unit 3 to the detector 2 may tilt relative to the horizontal direction. In this case, the rotation shaft 61 of the motor 6 is not limited to extend in the horizontal direction. The rotation shaft 61 may extend in the tilting direction relative to the horizontal direction.

The configuration of the optical member provided on the optical path of the measurement light from the light source unit 3 to the detector 2 is not limited to the configuration illustrated in the above embodiments. Another optical member may be provided, and a part of the optical members may be eliminated.

The scanning processing unit 101 is not limited to be configured to perform scanning by changing an angle at which measurement light emitted from a sample is received. The scanning processing unit 101 may be configured to perform scanning by changing an angle of measurement light incident on a sample. In this case, a collimator unit (not illustrated) holding a collimator lens may be fixed to a circular disc, and the disc may be rotated with a motor to perform scanning by changing an angle of the collimator unit to the V-block prism 1, for example.

The above embodiment describes that the present invention is applied to a V-block refractometer. However, the present invention is not limited to a V-block refractometer, and is applicable to a refractometer of another type, such as an Abbe refractometer.

DESCRIPTION OF REFERENCE SIGNS

1 V-block prism
2 detector
3 light source unit
4 first optical system
5 second optical system
6 motor
7 circular disc
8 mirror
9 lens
10 auto collimation prism
31 light source
32 mirror
41 lens
42, 43, 44 mirror
45 interference filter
46 slit
47 collimator lens
50 telemeter unit
51, 52 mirror
53 telemeter lens
54 beam splitter
61 rotation shaft
100 control unit
101 scanning processing unit
102 refractive index measurement processing unit
103 display processing unit
200 camera
300 display unit
301 display screen
311 graph
312 captured image
313 image-capture switch key
314 enlarged display key
315 start key
316 stop key

The invention claimed is:

1. A refractometer that measures a refractive index of a sample by irradiating the sample with measurement light, the refractometer comprising:
   a detector that detects an intensity of measurement light passing through the sample;
   a camera that captures an image of the measurement light passing through the sample; and
   a display processing unit that displays a graph indicating detection intensity of the measurement light detected by the detector and the image of the measurement light captured by the camera on one display screen in real time.

2. The refractometer according to claim 1, further comprising:
   a scanning processing unit that performs scanning by changing an angle at which measurement light emitted from the sample is received or an angle of measurement light incident on the sample, wherein
   the display processing unit displays detection intensity by the detector on the display screen in real time as being continuously depicted as a graph, the detection intensity being changed with scanning by the scanning processing unit, and the display processing unit also displays an image captured by the camera on the display screen in real time so as to move with scanning.

3. The refractometer according to claim 1, wherein the display processing unit displays on the display screen an image-capture switch key for starting or stopping a display of an image captured by the camera on the display screen.

4. The refractometer according to claim 1, wherein the display processing unit displays on the display screen an enlarged display key for enlarging and displaying an image captured by the camera on another screen on the display screen.

5. The refractometer according to claim 2, wherein the display processing unit displays on the display screen a stop key for stopping scanning by the scanning processing unit.

* * * * *